United States Patent
Gebhard-Hansen et al.

[11] Patent Number: 6,036,975
[45] Date of Patent: Mar. 14, 2000

[54] RAPID RELEASE TABLET COMPRISING TOLFENAMIC ACID OR A PHARMACEUTICALLY ACCEPTABLE SALT THEREOF

[75] Inventors: Knud Erik Gebhard-Hansen, Birekrød; Karen Bjørnsdottir, Værløse; Lars Hedevang Christensen, Copenhagen; Søren Bols Pedersen, Hvidovre, all of Denmark

[73] Assignee: A/S Gea Farmaceutisk Fabrik, Frederiksberg, Denmark

[21] Appl. No.: 09/091,526

[22] PCT Filed: Dec. 19, 1996

[86] PCT No.: PCT/DK96/00548

§ 371 Date: Jun. 19, 1998

§ 102(e) Date: Jun. 19, 1998

[87] PCT Pub. No.: WO97/22340

PCT Pub. Date: Jun. 26, 1997

[30] Foreign Application Priority Data

Dec. 20, 1995 [DK]  Denmark ................................ 1448/95

[51] Int. Cl.[7] .......................................................... A61K 9/20
[52] U.S. Cl. ........................ 424/465; 424/464; 424/470; 514/778; 514/779; 514/781; 514/951
[58] Field of Search ................................. 424/464, 465, 424/470, 468, 469

[56] References Cited

U.S. PATENT DOCUMENTS

B1 4,753,801   7/1992   Oren et al. ............................... 424/465

FOREIGN PATENT DOCUMENTS 116061    1/1976    Germany.
89/07439  8/1989    WIPO.
96/41617  12/1996   WIPO.

*Primary Examiner*—James M. Spear
*Attorney, Agent, or Firm*—Jacobson, Price, Holman & Stern, PLLC

[57] ABSTRACT

A rapid release tablet involves as an active ingredient tolfenamic acid or its pharmaceutically acceptable salts having a mean particle size of <10 μm, alginic acid or its pharmaceutically acceptable salts in an amount of 1.5–6.0% by weight, and a superdisintegrant in an amount of at least 6% by weight.

17 Claims, 2 Drawing Sheets

RAPID RELEASE TABLET COMPRISING TOLFENAMIC ACID OR A PHARMACEUTICALLY ACCEPTABLE SALT THEREOF

This application is a 371 of PCT/DK 96/00548 filed Dec. 19, 1996.

This invention relates to to a tablet comprising an active ingredient selected from tolfenamic acid and pharmaceutically acceptable salts thereof which is capable of rapid release of the active ingredient. In addition the invention relates to a method of preparing such tablet.

Tolfenamic acid, N-(2-methyl-3-chlorophenyl)-anthranilic acid, and salts thereof are known compounds having antiinflammatory and analgesic activity. The compounds and their aforementioned activities as well as a method of preparing the compounds have been described in DK patent no. 116 061.

During the treatment of patients suffering from rheumatic diseases with tolfenamic acid preparations some patients noticed a reduced occurrence of migraine attacks, and tolfenamic acid is now being marketed both as antiinflammatory and analgesic agent, particularly for the treatment of rheumatic diseases and dysmenorrhoea, and as anti-migraine agent (prophylactic as well as curative).

The tolfenamic acid preparations were originally formulated as capsules consisting of a hard gelatine capsule shell containing a loose powder of the tolfenamic acid in admixture with usual tablet and capsule fillers, the powder being made available for dissolution in the gastro-intestinal tract, when the gelatine capsule has been dissolved.

The capsule formulation was chosen because of difficulties in preparing a tablet containing a therapeutic dose and still being of a reasonable size, as a tablet of a size which could be easily swallowed by a patient, turned out to be very difficult to disintegrate.

Later efforts resulted in the development of tablets being capable of providing a bioavailability of the tolfenamic acid corresponding to that obtained by the tolfenamic acid capsules. Furthermore the maximum plasma concentration was found to be somewhat higher for the tablet formulation than for the capsule formulation. However, $T_{max}$, the time at which the maximum plasma concentration is obtained, was essentially unchanged.

The potential of zolfenamic acid of curing a migraine attack has accentuated the desire of obtaining a small tablet which is capable of providing a high plasma concentration of tolfenamic acid within a short time.

As a result of extensive research aiming at attaining this object, a tablet having these characteristics has now been developed. Thus a tablet has been provided, which is capable of providing a maximum plasma concentration of tolfenamic acid being almost twofold of that obtained with the capsule formulation (mean values of 5.60 µg/ml and 2.95 µg/ml, respectively, in a cross-over test carried out on 12 test persons), and furthermore within about half the time after administration ($T_{max}$ median values of 1.0 hours and 1.8 hours, respectively). As a further essential point, the mean plasma concentration reached half an hour after administration of the tablet according to the invention has been found to be more than twofold of that obtained by the known tablet, 2.60 µg/ml and 1.18 µg/ml, respectively. Thus a therapeutic level of tolfenamic acid is reached much faster by administration of the tablet according to the invention than by administration of the known tablet, among other things making the tablet according to the invention particularly suited for acute treatment of a migraine attack.

These surprising results are based on a selection of a particular combination of tablet formulation aids and a particular particle size of the active ingredient.

Accordingly the invention provides a tablet comprising an active ingredient selected from tolfenamic acid and pharmaceutically acceptable salts thereof, said active ingredient having a mean particle size of $\leq 10$ µm, and said tablet furthermore comprising alginic acid or a pharmaceutically acceptable salt thereof in an amount of 1.5–6.0% by weight and a superdisintegrant in an amount of at least 6% by weight.

The designation superdisintegrant refers to a group of disintegration agents being well-known to a person skilled in the art. Generally speaking, superdisintegrants are disintegration agents which can be used in a fractional amount of normal disintegrants to obtain the same effect. According to product information provided by the manufacturers of superdisintegrants, the superdisintegrants should be used in amounts of 1–8% with amounts of about 2% to about 4% being indicated as optimal. Thus the amounts of superdisintegrant used according to the invention are higher than the amounts generally used.

Cross-linked polyvinylpyrrolidones, particularly crospovidone, modified starches, particularly sodium starch glycolate, Starch 1500, modified celluloses, particularly croscarmellose sodium (cross-linked sodium carboxymethylcellulose), LHPC (Low substituted hydroxypropylcellulose) and Veegum are examples of preferred superdisintegrants for use in the tablet according to the invention.

Croscarmellose sodium is f.inst. commercialized under the trade name Ac-Di-Sol and sodium starch glycolate under the trade names Primojel and Explotab. Kollidon CL and Polyplasdone XL are commercial cross-linked PVP products.

According to the invention, the superdisintegrant will be present in the tablet in an amount of at least 6% by weight, such as in an amount at least 8% by weight, particularly in an amount of at least 10% by weight and preferably in an amount of at least 12% by weight. The superdisintegrant may be a single superdisintegrant or a combination of superdisintegrants and will normally be used in combination with one or more common disintegrants, such as starch, f. inst. corn starch.

There is no particular upper limit regarding the amount of superdisintegrant as long as the mechanical properties of the tablet are compatible with its intended use. However, normally the amount of superdisintegrant will not exceed 25% by weight. From a cost point of view, the amount of superdisintegrant will preferably not exceed 15–20% by weight as normally no particular benefits will be achieved beyond this range.

The superdisintegrant may be present as an extragranular and/or as an intragranular disintegration agent. According to one embodiment of the invention the superdisintegrant is present both as an intragranular disintegration agent and as an extragranular disintegration agent. Although the superdisintegrant may be present solely as an intragranular disintegration agent, it will in most cases be present as an extragranular disintegration agent, either solely as an extragranular disintegration agent or in combination with an intragranular disintegration agent as mentioned above.

The particle size of the active ingredient can be obtained in different ways, such as by milling or micronizing. The mean particle size can f.inst. be determined by the so-called Malvern technique, f.inst. using a Malvern Instrument of the type M6.10.

Typically milling results in a mean particle size in the upper half of the range from zero up to 10 μm whereas micronizing results in a mean particle size in the lower half of said range.

In a preferred embodiment of the invention, the mean particle size of the active ingredient is ≦8 μm.

A typical mean particle size of tolfenamic acid for use as active ingredient in the tablet according to the invention as obtained by milling is in the range from 5–7 μm with a specific surface area in the range from 1.0–1.2 $m^2/cm^3$, particularly in the range from 1.1–1.7 $m^2/cm^3$, as determined by the above mentioned Malvern technique.

A typical mean particle size of tolfenamic acid for use as active ingredient in the tablet according to the invention as obtained by micronizing is in the range from 1.5–2.5 μm with a specific surface area in the range from 2.5–3.5 $m^2/cm^3$, as determined by the Malvern technique.

Generally the specific surface area of the active ingredient will be in the range from 1.0–4.0 $m^2/cm^3$.

As the micronizing process is more expensive than milling and no particular advantages seem to be obtained by a micronized product compared to a milled product, the latter is normally preferred from a cost point of view.

The very hydrophobic nature of tolfenamic acid necessitates the use of an agent being capable of reducing the hydrophobicity of the particles, and alginic acid and pharmaceutically acceptable salts thereof have been found particularly suited for that purpose. Thus a dissolution of 86% of the tolfenamic acid included in a tablet as active ingredient has been obtained within 3 minutes by use of alginic acid as granulation agent compared to 32% and 47%, respectively, by use of the conventional granulation agents, polyvinylpyrrolidone and gelatine.

Similarly milling or micronizing results in an increase of the dissolution within 3 minutes by about two thirds compared to an unmilled product. Thus also the particle size appears to be of importance.

Finally the use of a superdisintegrant in an amount of at least 6% by weight has turned out to be an important feature for obtaining the desired rapid release of the active ingredient.

The alginic acid or pharmaceutically acceptable salt thereof is generally included in an amount of 1.5 –6.0% by weight and preferably in an amount of 2.5–5.0% by weight.

Alkali metal salts, such as the sodium and potassium salts, are examples of pharmaceutically acceptable salts of alginic acid which may be used according to the invention.

In a preferred embodiment of the invention the alginic acid or pharmaceutically acceptable salt thereof is used as a granulation agent in the preparation of the tablet.

A presently preferred embodiment of the invention relates to a tablet comprising from 40–70% by weight of the active ingredient, from 2.5–5.0% by weight of alginic acid or a pharmaceutically acceptable salt thereof, from 6–10% by weight of intragranular sodium starch glycolate, from 3–5% by weight of extragranular sodium starch glycolate and from 1–3% by weight of extragranular croscarmellose sodium, the remainder up to 100% by weight consisting of conventional tablet formulation aids, such as fillers, binding agents, disintegrants, lubricants, etc.

In a further aspect of the invention a method of preparing a tablet as indicated above is provided, said method comprising the following steps:

a) blending an active ingredient selected from tolfenamic acid and pharmaceutically acceptable salts thereof having a mean particle size of ≦10 μm with a disintegration agent and optionally other intragranular tablet formulation aids, b) kneading the resulting blend with a solution or dispersion of alginic acid or a pharmaceutically acceptable salt thereof to form a moist homogeneous mass, the alginic acid or pharmaceutically acceptable salt thereof being used in an amount to give a concentration thereof in the resulting tablet of 1.5–6.0% by weight, and granulating the moist homogeneous mass, c) drying the obtained granules, optionally after blending with a filler and/or other tablet formulation aids, d) blending the dried granules with a disintegration agent and optionally other extragranular tablet formulation aids, and e) compressing the resulting blend into a tablet, with the proviso that the disintegration agent used in step a) and/or step d) comprises one or more superdisintegrants in a total amount to give a concentration of superdisintegrant in the resulting tablet of at least 6% by weight.

The invention also relates to the use of tolfenamic acid or a pharmaceutically acceptable salt thereof having a mean particle size of ≦10 μm in combination with alginic acid or a pharmaceutically acceptable salt thereof and a superdisintegrant for the preparation of a tablet for treatment of pain, inflammation, migraine, dysmenorrhoea and fever, particularly for acute treatment thereof, the alginic acid or pharmaceutically acceptable salt thereof and the superdisintegrant being used in amounts of 1.5–6.0% by weight and at least 6% by weight, respectively.

The tablets according to the invention comprising tolfenamic acid or a pharmaceutically acceptable salt thereof as active ingredient will usually be administered in a daily dose corresponding to 200–600 mg of tolfenamic acid with a unit dose of 200 mg per tablet. Using the formulation according to the invention, a rapid release tablet containing such unit dose of 200 mg can be made with a total weight as low as about 350 –375 mg. If desired, the tablets according to the invention can also be prepared to contain multiples of such unit doses, in which case the tablets will be provided with means such as notches for easy division into suitable parts. F.inst. tablets containing a double dose and being provided with a notch for easy division into two halves can be prepared. Also tablets containing a single dose can be notched for easy division, if desired. Furthermore the tablets can be provided with identification codes.

In a preferred aspect, the invention provides a tablet comprising a unit dose of tolfenamic acid or a pharmaceutically acceptable salt thereof, of about 200 mg tolfenamic acid, or a multiple of such unit dose, and having a total weight of 350–400 mg per unit dose, preferably about 375 mg per unit dose.

As a further preferred aspect, the invention provides a tablet being capable of providing a mean plasma concentration of tolfenamic acid of about 2.00 μg/ml within half an hour after administration.

Figure 1:
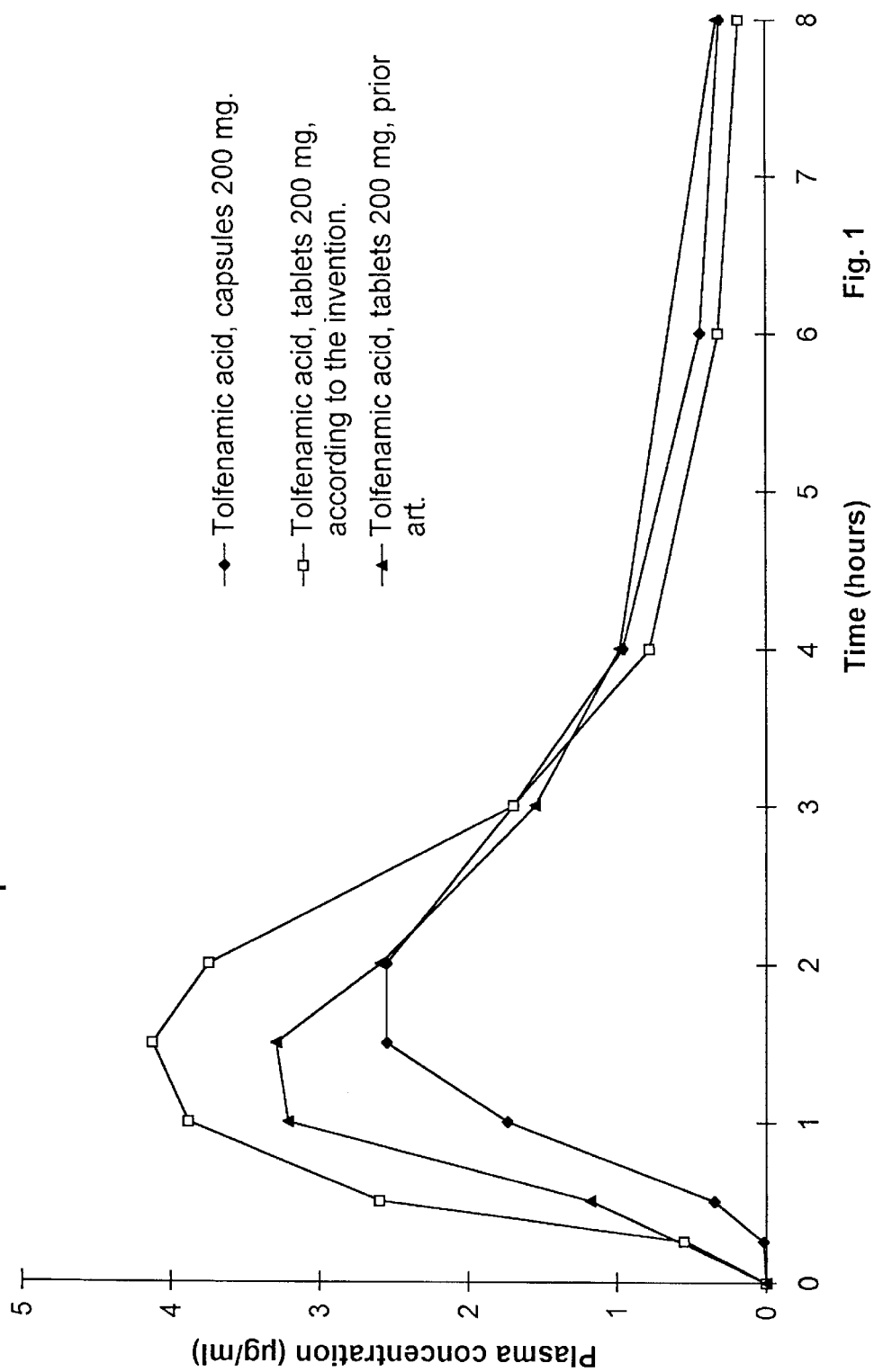
FIG. 1 illustrates mean plasma concentration curves for tolfenamic acid tablets according to the invention and tolfenamic acid capsules and tablets according to the prior art, and FIG. 2 dissolution curves for the same tolfenamic acid preparations.

In the following the tablet of the invention and its method of preparation will be further illustrated by examples which should not be regarded as limiting.

EXAMPLE 1

Rapid release tablets, each containing 200 mg of tolfenamic acid as active ingredient, were prepared using the following ingredients and procedure.

|      | Ingredients | Amount |
|------|-------------|--------|
| I.   | Tolfenamic acid milled to a mean particle size of about 5.7 μm | 1000 g |
|      | Amyl. maidis (corn starch) | 320 - |
|      | Sodium starch glycolate | 150 - |
| II.  | Alginic acid | 60 g |
|      | Aq. purificata 100° C. | 500 - |
|      | Aq. purificata 10–12° C. | 750 - |
| III. | Cellulose, microcrystalline | ad 1530 g |
| IV.  | Cellulose, microcrystalline | 120 g |
|      | Polyethylene glycol 6000 | 75 - |
|      | Croscarmellose sodium | 35 - |
|      | Silicium dioxide | 10 - |
|      | Sodium starch glycolate | 75 - |
|      | Sodium stearyl fumarate | 15 - |

I is blended in a suitable intensive blender for 60 sec. after which the prepared solution II is added and worked into I until adequate wetting.

The wet mass of I+II is passed through a screen having a mesh width of 2.5 mm (8 mesh). Then the prepared granules are dried to a weight of 1480–1530 g in a suitable fluidizer and supplemented to 1530 g with III as necessary.

After drying the granules are screened on a screen having a mesh width of 1.5 mm (12 mesh).

The ingredients under IV are screened on a screen having a mesh width of 0.15 mm (100 mesh) and then added to the dry-screened granules in a suitable mixing apparatus for final mixing.

The resulting granules are formed into tablets of a gross weight of 372 mg and containing 200 mg of tolfenamic acid each, using oval matrices of 7×14 mm optionally provided with a dividing notch and an identification code on one of its faces.

The above amounts are adequate for the preparation of 5000 tablets.

EXAMPLE 2

Using the same procedure as described in example 1 tablets of the following content were prepared.

| Tolfenamic acid, milled to a mean particle size of about 6.2 μm | 200 mg |
|---|---|
| Amylum maidis | 64 - |
| Sodium starch glycolate | 22.5 - |
| Polyethylene glycol | 15 - |
| Alginic acid | 12 - |
| Cellulose, microcrystalline | 24 - |
| Croscarmellose sodium A | 5.25 - |
| Silicium dioxide | 2 - |
| Sodium starch glycolate | 11.25 - |
| Sodium stearyl fumarate | 3 - |

Comoarative Example 1
Preparation of Tolfenamic Acid Capsules According to the Prior Art Capsules, each containing 200 mg of tolfenamic acid as active ingredient, were prepared using the following ingredients and procedure.

|      | Ingredients | Amount |
|------|-------------|--------|
| I.   | Tolfenamic acid, unmilled | 1000 g |
|      | Lactose | 403.5 - |
|      | Amyl. maidis | 167.5 - |
| II.  | Polyvinylpyrrolidone | 16.5 g |
|      | Ethanol | 160.0 - |
|      | Aq. purificata | 200.0 - |
| III. | Amyl. maidis | ad 1587.5 g |
| IV.  | Polyethlene glycol 6000 | 75.0 g |
|      | Talc | 87.5 - |

I is blended in a suitable intensive blender for 60 sec. after which the prepared solution II is added and worked into I until adequate wetting.

The wet mass of I+II is passed through a screen having a mesh width of 2.5 mm (8 mesh). Then the prepared granules are dried to a weight of 1550–1587.5 g in a suitable fluidizer and supplemented to 1587.5 g with III as necessary.

After drying the granules are screened on a screen having a mesh width of 1.0 mm (18 mesh).

The ingredients under IV are screened on a screen having a mesh width of 0.15 mm (100 mesh) and then added to the dry-screened granules in a suitable mixing apparatus for final mixing.

The resulting granules are filled into hard gelatine capsules of size 2 in an amount of 350 mg/capsule corresponding to 200 mg tolfenamic acid/capsule, using a suitable capsule filling apparatus.

The above amounts are adequate for the preparation 5000 capsules.

Comparative Example 2
Preparation of Tolfenamic Acid Tablets According to the Prior Art Tablets, each containing 200 mg of tolfenamic acid as active ingredient, were prepared using the following ingredients and procedure.

|      | Ingredients | Amount |
|------|-------------|--------|
| I.   | Tolfenamic acid, unmilled | 1000 g |
|      | Lactose | 250 - |
|      | Amyl. maidis | 300 - |
| II.  | Polyvinylpyrrolidone | 75 g |
|      | Ethanol | 80 - |
|      | Aq. purificata | 100 - |
| III. | Amyl. maidis | ad 1625 g |
| IV.  | Cellulose, microcrystalline | 100 g |
|      | Silicium dioxide | 10 - |
|      | Croscarmellose sodium | 35 - |
|      | Sodium stearyl fumarate | 15 - |
|      | Polyethylene glycol 6000 | 75 - |

I is blended in a suitable intensive blender for 60 sec. after which the prepared solution II is added and worked into I until adequate wetting.

The wet mass of I+II is passed through a screen having a mesh width of 2.5 mm (8 mesh). Then the prepared granules are dried to a weight of 1600–1625 g in a suitable fluidizer and supplemented to 1625 g with III as necessary.

After drying the granules are screened on a screen having a mesh width of 1.5 mm (12 mesh).

The ingredients under IV are screened on a screen having a mesh width of 0.15 mm (100 mesh) and then added to the dry-screened granules in a suitable mixing apparatus for final mixing.

The resulting granules are formed into tablets of a gross weight of 372 mg and containing 200 mg of tolfenamic acid each, using oval matrices of 7×14 mm optionally provided with a dividing notch and an identification code on one of its faces.

The above amounts are adequate for the preparation of 5000 tablets.

Comparative Example 3

Bioavailability Studies

Tolfenamic acid tablets according to the invention, prepared as described in example 1 and tolfenamic acid capsules prepared as described in comparative example 1 were compared as to bioavailability of tolfenamic acid after oral administration, in a randomized single dose cross-over study carried out on 12 healthy volunteers.

Blood samples were collected after ¼, ½, 1, 1 ½, 2, 3, 4, 6 and 8 hours and the plasma concentration of tolfenamic acid in µg/ml was determined. The individual results are listed in tables Ia and IIa below, together with the mean and SEM values of the plasma concentrations obtained after ¼, ½, 1 hour etc.

TABLE Ia

Tolfenamic acid tablets 200 mg, according to the invention.

| Subject No. Time (h) | ¼ | ½ | 1 | 1½ | 2 | 3 | 4 | 6 | 8 |
|---|---|---|---|---|---|---|---|---|---|
| 1 | <0.05 | 0.07 | 0.44 | 4.68 | 6.57 | 1.98 | 0.68 | 0.21 | 0.12 |
| 2 | 3.16 | 5.21 | 6.39 | 4.18 | 2.48 | 1.51 | 0.54 | 0.52 | 0.20 |
| 3 | <0.05 | 3.08 | 5.97 | 4.61 | 3.05 | 0.92 | 0.93 | 0.57 | 0.14 |
| 4 | 0.00 | 0.76 | 4.49 | 4.43 | 2.00 | 0.78 | 0.28 | 0.14 | 0.11 |
| 5 | 0.26 | 0.74 | 3.77 | 7.10 | 5.98 | 2.89 | 1.65 | 0.42 | 0.33 |
| 6 | 1.91 | 5.79 | 4.21 | 3.08 | 2.15 | 1.06 | 0.64 | 0.17 | 0.08 |
| 7 | 0.14 | 2.56 | 5.35 | 4.86 | 3.21 | 1.80 | 0.64 | 0.33 | 0.17 |
| 8 | 0.19 | 4.30 | 4.26 | 1.70 | 0.78 | 0.60 | 0.24 | 0.32 | 0.15 |
| 9 | 0.00 | 0.09 | 0.23 | 3.32 | 5.99 | 2.49 | 1.13 | 0.18 | 0.20 |
| 10 | <0.05 | 1.92 | 2.65 | 2.01 | 2.92 | 0.90 | 0.29 | 0.12 | 0.11 |
| 11 | <0.05 | 1.92 | 4.30 | 6.52 | 7.63 | 4.36 | 1.87 | 0.48 | 0.45 |
| 12 | 0.95 | 4.70 | 4.44 | 2.96 | 2.09 | 1.06 | 0.41 | 0.32 | 0.12 |
| Mean | 0.55 | 2.60 | 3.88 | 4.12 | 3.74 | 1.70 | 0.78 | 0.32 | 0.18 |
| SEM | 0.29 | 0.58 | 0.55 | 0.47 | 0.64 | 0.32 | 0.15 | 0.04 | 0.03 |

TABLE IIa

Tolfenamic acid Capsules 200 mg.

| Subject No. Time (h) | ¼ | ½ | 1 | 1½ | 2 | 3 | 4 | 6 | 8 |
|---|---|---|---|---|---|---|---|---|---|
| 1 | 0.00 | 0.00 | 1.88 | 3.66 | 3.88 | 2.12 | 0.95 | 0.23 | 0.17 |
| 2 | 0.22 | 1.27 | 3.47 | 4.16 | 4.24 | 2.36 | 0.94 | 0.22 | 0.25 |
| 3 | <0.05 | 0.14 | 1.63 | 5.35 | 5.04 | 1.82 | 0.78 | 0.14 | 0.07 |
| 4 | 0.00 | 0.00 | 0.19 | 0.63 | 0.53 | 1.42 | 1.78 | 0.43 | 0.26 |
| 5 | 0.00 | 0.32 | 3.30 | 3.94 | 3.54 | 2.16 | 1.48 | 0.38 | 0.21 |
| 6 | 0.00 | 0.13 | 2.47 | 3.45 | 3.06 | 1.61 | 0.55 | 0.55 | 0.20 |
| 7 | 0.00 | 0.70 | 2.43 | 2.50 | 2.00 | 2.03 | 0.97 | 0.32 | 0.15 |
| 8 | 0.00 | 0.06 | 0.32 | 1.17 | 1.46 | 2.06 | 0.89 | 0.38 | 0.19 |
| 9 | <0.05 | 0.18 | 1.69 | 2.13 | 2.02 | 1.42 | 1.05 | 0.72 | 0.31 |
| 10 | <0.05 | 0.86 | 1.69 | 1.88 | 2.68 | 1.27 | 0.56 | 0.15 | 0.15 |
| 11 | 0.00 | 0.00 | 0.00 | <0.05 | 0.09 | 0.32 | 0.57 | 1.19 | 1.58 |
| 12 | 0.00 | 0.53 | 1.84 | 1.70 | 1.76 | 1.81 | 0.70 | 0.61 | 0.21 |
| Mean | 0.02 | 0.35 | 1.74 | 2.55 | 2.55 | 1.70 | 0.96 | 0.44 | 0.31 |
| SEM | 0.02 | 0.12 | 0.32 | 0.46 | 0.42 | 0.16 | 0.10 | 0.09 | 0.12 |

In table IIIa below the maximum plasma concentration, $C_{max}$, and the area under the plasma concentration curve, $AUC_{0\to\infty}$, for each test person are listed together with the mean and SEM values.

TABLE IIIa

| | Tolfenamic acid tablet, 200 mg, according to the invention | | Tolfenamic acid capsule, 200 mg, prior art | |
|---|---|---|---|---|
| Subject No. | $C_{max}$ µg/ml | $AUC_{0-\infty}$ (µg/ml)h | $C_{max}$ µg/ml | $AUC_{0-\infty}$ (µg/ml)h |
| 1 | 6.57 | 11.61 | 3.88 | 11.12 |
| 2 | 6.39 | 14.01 | 4.24 | 13.53 |
| 3 | 5.97 | 12.65 | 5.35 | 10.61 |
| 4 | 4.49 | 8.14 | 1.78 | 7.06 |
| 5 | 7.10 | 17.60 | 3.94 | 12.53 |
| 6 | 5.79 | 10.37 | 3.45 | 10.43 |
| 7 | 5.35 | 12.45 | 2.50 | 9.16 |
| 8 | 4.30 | 7.65 | 2.06 | 6.97 |
| 9 | 5.99 | 11.93 | 2.13 | 10.25 |
| 10 | 2.92 | 7.21 | 2.68 | 7.02 |
| 11 | 7.63 | 21.69 | 1.58 | 16.56 |
| 12 | 4.70 | 9.97 | 1.84 | 8.18 |
| Mean | 5.60 | 12.11 | 2.95 | 10.29 |
| SEM | 0.38 | 1.21 | 0.35 | 0.84 |

As will be seen, the tablet according to the invention results in a maximum plasma concentration being almost twofold of that obtained by the capsule formulation (5.60 µg/ml vs. 2.95 µg/ml). In addition, the total area under the plasma concentration curve appears to be larger for the tablet according to the invention than for the capsule preparation, indicating that the tolfenamic acid is utilized more efficiently in the tablet according to the invention than in the capsule formulation.

As a further important feature, the maximum plasma concentration is obtained in a much shorter time ($T_{max}$ median values of 1.0 hours and 1.8 hours, respectively), as will appear from table IVa below wherein the time, $T_{max}$, for each test person to reach $C_{max}$ is listed together with the median value.

TABLE IVa

| Subject No. | Tolfenamic acid tablet, 200 mg, according to the invention, $T_{max}$ (h) | Tolfenamic acid capsule, 200 mg, prior art, $T_{max}$ (h) |
|---|---|---|
| 1 | 2.0 | 2.0 |
| 2 | 1.0 | 2.0 |
| 3 | 1.0 | 1.5 |
| 4 | 1.0 | 4.0 |
| 5 | 1.5 | 1.5 |
| 6 | 0.5 | 1.5 |
| 7 | 1.0 | 1.5 |
| 8 | 0.5 | 3.0 |
| 9 | 2.0 | 1.5 |
| 10 | 2.0 | 2.0 |
| 11 | 2.0 | 8.0 |
| 12 | 0.5 | 1.0 |
| Median | 1.0 | 1.8 |

In a corresponding randomized single dose cross-over study carried out on 12 healthy volunteers, tolfenamic acid tablets according to the prior art prepared as described in comparative example 2 was compared to the capsule formulation prepared in comparative example 1 with the results indicated in tables Ib–IVb below, table Ib corresponding to the above table Ia, etc.

TABLE Ib

Tolfenamic acid tablets 200 mg, prior art.

| Subject No. | Plasma concentration, µg/ml | | | | | | |
|---|---|---|---|---|---|---|---|
| Time (h) | ½ | 1 | 1½ | 2 | 3 | 4 | 8 |
| 1 | 0.58 | 3.09 | 4.12 | 2.48 | 1.44 | 0.59 | 0.24 |
| 2 | 2.80 | 6.56 | 4.32 | 3.08 | 1.11 | 0.85 | 0.19 |
| 3 | 3.26 | 5.79 | 4.48 | 2.98 | 1.20 | 0.49 | 0.29 |
| 4 | 2.37 | 3.67 | 3.64 | 2.25 | 1.18 | 1.30 | 0.39 |
| 5 | 0.77 | 1.94 | 2.71 | 2.55 | 2.64 | 1.52 | 0.54 |
| 6 | 0.09 | 2.27 | 3.20 | 2.28 | 1.50 | 0.79 | 0.19 |
| 7 | 0.42 | 1.87 | 2.04 | 1.58 | 1.29 | 0.45 | 0.18 |
| 8 | 0.80 | 3.22 | 3.36 | 2.92 | 1.77 | 1.15 | 0.27 |
| 9 | 1.11 | 4.30 | 3.25 | 1.85 | 0.80 | 0.45 | 0.25 |
| 10 | 0.19 | 1.58 | 2.89 | 2.95 | 2.76 | 2.19 | 0.61 |
| 11 | 1.17 | 3.01 | 3.75 | 2.86 | 1.66 | 1.30 | 0.26 |
| 12 | 0.57 | 1.23 | 1.76 | 3.30 | 1.17 | 0.70 | 0.60 |
| Mean | 1.18 | 3.21 | 3.29 | 2.59 | 1.55 | 0.98 | 0.33 |
| SEM | 0.30 | 0.48 | 0.24 | 0.15 | 0.17 | 0.15 | 0.05 |

TABLE IIb

Tolfenamic acid Capsules 200 mg.

| Subject No. | Plasma concentration, µg/ml | | | | | | |
|---|---|---|---|---|---|---|---|
| Time (h) | ½ | 1 | 1½ | 2 | 3 | 4 | 8 |
| 1 | 0.07 | 0.29 | 2.04 | 2.31 | 1.66 | 1.67 | 0.36 |
| 2 | 3.22 | 4.68 | 3.55 | 2.21 | 0.72 | 0.46 | 0.17 |
| 3 | 0.22 | 2.31 | 2.18 | 2.15 | 1.46 | 1.39 | 0.35 |
| 4 | 1.19 | 3.21 | 2.49 | 2.08 | 1.57 | 0.03 | 0.45 |
| 5 | 0.00 | 1.50 | 1.66 | 1.64 | 1.91 | 1.12 | 0.36 |
| 6 | 0.39 | 1.23 | 1.61 | 1.29 | 1.38 | 0.97 | 0.19 |
| 7 | 2.09 | 2.35 | 1.58 | 0.98 | 0.57 | 0.49 | 0.33 |
| 8 | 0.25 | 1.83 | 2.57 | 2.28 | 1.65 | 0.98 | 0.38 |
| 9 | 0.00 | 0.28 | 1.00 | 1.08 | 1.16 | 0.95 | 0.86 |
| 10 | 0.42 | 0.99 | 1.45 | 2.13 | 2.34 | 2.76 | 0.55 |
| 11 | 0.47 | 1.72 | 2.05 | 1.88 | 1.24 | 1.07 | 0.27 |
| 12 | 0.12 | 2.79 | 3.50 | 3.36 | 1.74 | 1.31 | 0.51 |
| Mean | 0.70 | 1.93 | 2.14 | 1.95 | 1.45 | 1.18 | 0.40 |
| SEM | 0.29 | 0.86 | 0.23 | 0.19 | 0.14 | 0.17 | 0.05 |

TABLE IIIb

| | Tolfenamic acid tablet, 200 mg, prior art | | Tolfenamic acid capsule, 200 mg, prior art | |
|---|---|---|---|---|
| Subject No. | Cmax (µg/ml) | AUC 0–26 h (µg/ml)h | Cmax (µg/ml) | AUC 0–26 h (µg/ml)h |
| 1 | 4.12 | 11.36 | 2.31 | 13.36 |
| 2 | 6.56 | 14.86 | 4.68 | 11.73 |
| 3 | 5.79 | 15.12 | 2.31 | 13.39 |
| 4 | 3.67 | 15.04 | 3.21 | 14.06 |
| 5 | 2.71 | 16.89 | 1.91 | 12.19 |
| 6 | 3.20 | 9.87 | 1.61 | 8.58 |
| 7 | 2.04 | 7.58 | 2.35 | 8.84 |
| 8 | 3.36 | 13.69 | 2.57 | 12.59 |
| 9 | 4.30 | 10.84 | 1.16 | 14.36 |
| 10 | 2.96 | 19.25 | 2.76 | 18.45 |
| 11 | 3.75 | 13.82 | 2.05 | 10.55 |
| 12 | 3.30 | 15.06 | 3.50 | 16.66 |
| Mean | 3.81 | 13.62 | 2.54 | 12.90 |
| SEM | 0.37 | 0.93 | 0.27 | 0.83 |

TABLE IVb

| Subject No. | Tolfenamic acid tablet, 200 mg, prior art, $T_{max}$ (h) | Tolfenamic acid capsule, 200 mg, prior art, $T_{max}$ (h) |
|---|---|---|
| 1 | 1.5 | 2.0 |
| 2 | 1.0 | 1.0 |
| 3 | 1.0 | 1.0 |
| 4 | 1.0 | 1.0 |
| 5 | 1.5 | 3.0 |
| 6 | 1.5 | 1.5 |
| 7 | 1.5 | 1.0 |
| 8 | 1.5 | 1.5 |
| 9 | 1.0 | 3.0 |
| 10 | 2.0 | 4.0 |
| 11 | 1.5 | 1.5 |
| 12 | 2.0 | 1.5 |
| Median | 1.5 | 1.5 |

Although the tablet according to the prior art results in a somewhat higher maximum plasma concentration than the capsule preparation, 3.81 µg/ml vs. 2.54 µg/ml, cf. table IIIb, the increase is much smaller than that obtained by the tablet according to the invention, resulting in an increase from 2.95 µg/ml to 5.60 µg/ml, as indicated in the above table IIIa. Furthermore, the prior art tablet has the same $T_{max}$ median value as the capsule preparation.

Thus the tolfenamic acid tablet according to the invention results in a substantively increased maximum plasma concentration being obtained in a substantively reduced period of time, not only compared to the known capsule preparation but also compared to the known tolfenamic acid tablet. Furthermore the tablet according to the invention results in a higher total area under the plasma concentration curve that the two other preparations meaning that a higher utilization of the active ingredient can be achieved.

The above results are further illustrated in FIG. 1 wherein mean plasma concentration curves for the three preparations are shown.

Dissolution Tests

The dissolution tests are carried out according to Ph.Eur. V.5.4 using a paddle apparatus operating at 100 rpm.

Initially the following solution is prepared: 40.8 g $KH_2PO_4$ is dissolved in 1500 ml of water. pH is adjusted to 7.2 with NaOH (40%) and 4500 ml of water is added.

The tablet/capsule to be tested is added to 1000 ml medium of 37° C. prepared by diluting 150 ml 96% ethanol to 1000 ml with the above solution. After 3, 5, 10, 15, 30 and 60 minutes 10 ml samples are withdrawn and analyzed by UV spectrophotometry at 289 nm using medium as reference and a solution of 25 mg tolfenamic acid in 50.00 ml 0.1 N NaOH diluted 2→100 with medium as standard.

Figure 2:
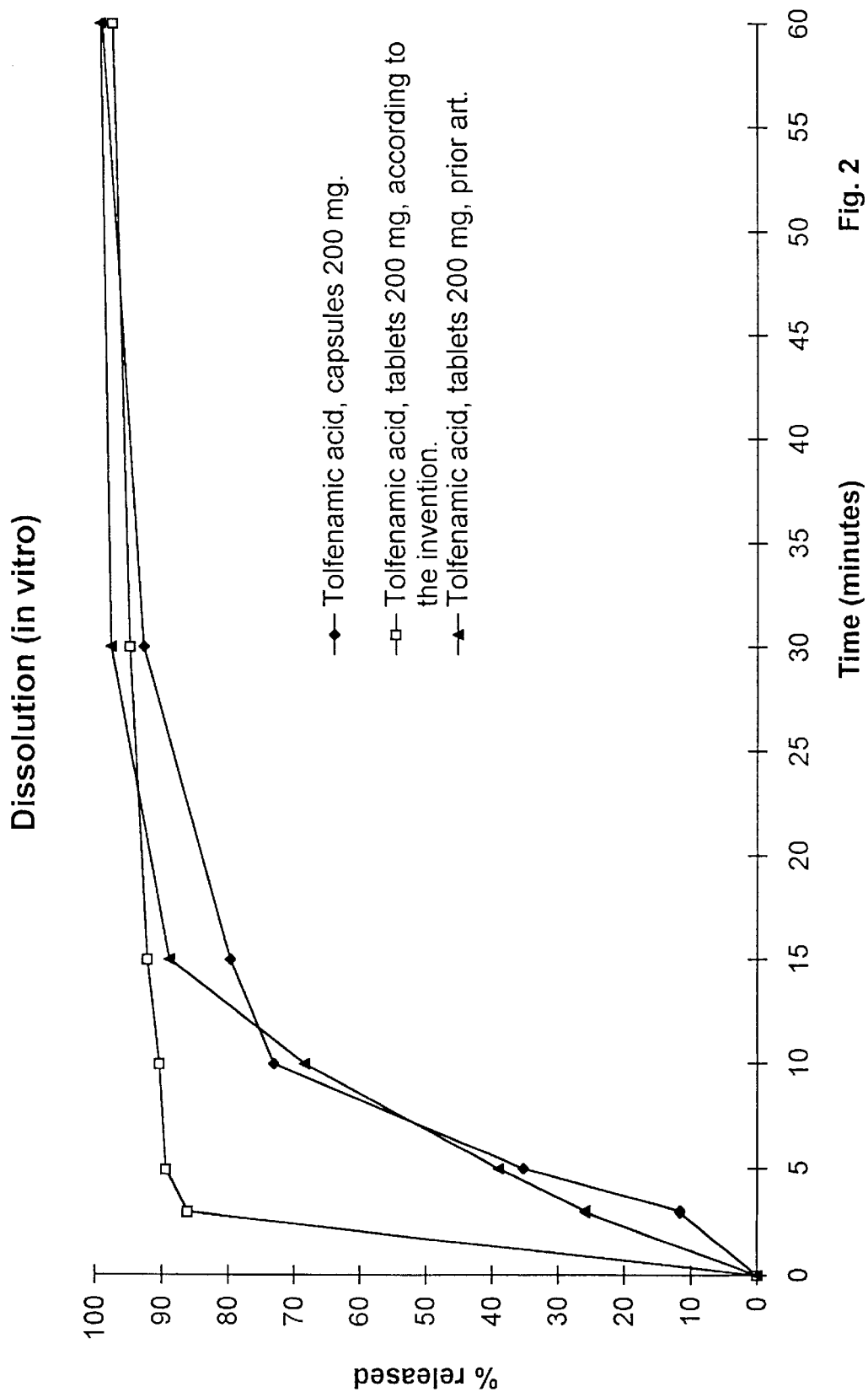

In FIG. 2 dissolution curves for the tablet according to the invention and the prior art tablet and capsule formulations are shown. The much faster dissolution of the tablet according to the invention is evident.

In the preceding the invention has been described by means of specific examples of preferred embodiments. However it will be appreciated, that various modifications can be made by a person skilled in the art without deviating from the spirit and scope of the invention.

We claim:

1. A tablet comprising an active ingredient selected from tolfenamic acid and pharmaceutically acceptable salts thereof, said active ingredient having a mean particle size of ≦10 µm, and said tablet furthermore comprising alginic acid or a pharmaceutically acceptable salt thereof in an amount of 1.5–6.0% by weight and a superdisintegrant in an amount of at least 6% by weight.

2. A tablet according to claim 1, wherein the superdisintegrant is present as an extragranular disintegration agent.

3. A tablet according claim 1, wherein the superdisintegrant is present both as an intragranular disintegration agent and as an extragranular disintegration agent.

4. A tablet according to claim 1, wherein the alginic acid or the pharmaceutically acceptable salt thereof is included as a granulation agent.

5. A tablet according to claim 1, wherein the particle size of the active ingredient has been provided by milling or micronizing.

6. A tablet according to claim 1, wherein the specific surface area of the active ingredient is in the range from $1.0–4.0 \text{ m}^2/\text{cm}^3$.

7. A tablet according to claim 1, being capable of providing a mean plasma concentration of tolfenamic acid of about 2.00 μg/ml within half an hour after administration.

8. A method of treating pain, inflamation, migraine, dysmenorrhoea, or fever comprising administering to a patient the tablet according to claim 1.

9. A tablet according to claim 1, wherein the superdisintegrant is selected from a cross-linked polyvinylpyrrolidone, a modified starch, a modified cellulose, and aluminum magresium silicate.

10. A tablet according to claim 1, wherein the superdisintegrant is present in an amount of at least 8% by weight.

11. A tablet according to claim 1, comprising from 40–70% by weight of the active ingredient, from 2.5–5.0% by weight of alginic acid or a pharmaceutically acceptable salt thereof, from 6–10% by weight of intragranular sodium starch glycolate, from 3–5% by weight of extragranular sodium starch glycolate and from 1–3% by weight of extragranular croscarmellose sodium, the remainder up to 100% by weight consisting of conventional tablet formulation aids.

12. A tablet according to any one of the preceding claims comprising a unit dose of tolfenamic acid or a pharmaceutically acceptable salt thereof, of about 200 mg tolfenamic acid, or a multiple of such unit doses, and having a total weight of 350–400 mg per unit dose.

13. A method of preparing a tablet according to claim 1, comprising the following steps:

a) blending an active ingredient selected from tolfenamic acid and pharmaceutically acceptable salts thereof having a mean particle size of $\leq 10$ μm with a disintegration agent and optionally additional intragranular tablet formulation aids, b) kneading the resulting blend with a solution or dispersion of alginic acid or a pharmaceutically acceptable salt thereof to form a moist homogeneous mass, the alginic acid or pharmaceutically acceptable salt thereof being used in an amount to give a concentration thereof in the resulting tablet of 1.5–6.0% by weight, and granulating the moist homogeneous mass, c) drying the obtained granules, optionally after blending with a filler and/or additional tablet formulation aids, d) blending the dried granules with a disintegration agent and optionally additional extragranular tablet formulation aids, and e) compressing the resulting blend into a tablet, with the proviso that the disintegration agent used in step a) and/or step d) comprises one or more superdisintegrants in a total amount to give a concentration of superdisintegrant in the resulting tablet of at least 6% by weight.

14. A tablet according to claim 9, wherein the cross-linked polyvinylpyrrolidone is crospovidone, the modified starch is sodium starch glycolate or pregelatinized Starch, and the modified cellulose is croscarmellose sodium or low substituted hydroxypropylcellulose.

15. A tablet according to claim 11, wherein the superdisintegrant is present in an amount of at least 10% by weight.

16. A tablet according to claim 11, wherein the superdisintegrant is present in an amount of at least 12% by weight.

17. A tablet according to claim 11, having a total weight of about 375 mg per unit dose.

* * * * *